United States Patent
Dellimore et al.

(10) Patent No.: US 10,332,423 B2
(45) Date of Patent: Jun. 25, 2019

(54) CARDIOPULMONARY RESUSCITATION GUIDANCE METHOD, COMPUTER PROGRAM PRODUCT AND SYSTEM

(71) Applicant: KONINKLIJKE PHILIPS N.V., Eindhoven (NL)

(72) Inventors: Kiran Hamilton J. Dellimore, Ut (NL); Jens Muehlsteff, Aachen (DE)

(73) Assignee: KONINKLIJKE PHILIPS N.V.V, Eindhoven (NL)

( * ) Notice: Subject to any disclaimer, the term of this patent is extended or adjusted under 35 U.S.C. 154(b) by 0 days.

(21) Appl. No.: 15/577,390

(22) PCT Filed: May 16, 2016

(86) PCT No.: PCT/EP2016/060933
§ 371 (c)(1),
(2) Date: Nov. 28, 2017

(87) PCT Pub. No.: WO2016/188780
PCT Pub. Date: Dec. 1, 2016

(65) Prior Publication Data
US 2018/0174489 A1      Jun. 21, 2018

(30) Foreign Application Priority Data

May 28, 2015   (EP) .................................. 15169581
Jun. 30, 2015   (EP) .................................. 15174415

(51) Int. Cl.
G08B 23/00        (2006.01)
G09B 23/28        (2006.01)
(Continued)

(52) U.S. Cl.
CPC .......... G09B 23/288 (2013.01); A61B 5/0077 (2013.01); A61B 5/02438 (2013.01);
(Continued)

(58) Field of Classification Search
CPC ....... G09B 23/288; A61B 5/02; A61B 5/6803; G06K 9/00342; G08B 23/00
See application file for complete search history.

(56) References Cited

U.S. PATENT DOCUMENTS 8,034,006 B2    10/2011   Celik-Butler et al.
2008/0171311 A1    7/2008   Centen et al.
(Continued)

FOREIGN PATENT DOCUMENTS

EP    2308450 A1    4/2011
EP    2851831 A1    3/2015
(Continued)

OTHER PUBLICATIONS

Go et al: "Heart Disease and Stroke Statistics—2013 Update", A Report From the American Heart Association, Circulation, 2013;127:000-000, pp. e1-e240.
(Continued)

*Primary Examiner* — Phung Nguyen

(57) ABSTRACT

A hands-free cardiopulmonary resuscitation (CPR) guidance method (40) for a system including a head-mountable computing device (100) comprising a processor (110) and at least one display module (106, 106') arranged to be viewed by the wearer (20) of the head-mountable computing device when wearing the device is disclosed that allows a rescuer to receive CPR guidance without losing sight of the victim. The method comprises receiving (420), on said processor, a first signal conveying vital signs information from at least one sensor (200, 210) for monitoring vital signs of a patient (10), wherein a sensor (210) of the at least one sensor is integrated in the head-mountable computing device (100); processing said first signal on said processor to obtain the vital signs information; and displaying (422) CPR guidance on said at least one display module in response to the processed vital signs information. A computer program
(Continued)

product and a CPR guidance system are also disclosed. The system may be created in situ using ubiquitous devices, e.g. smart devices including usable sensors, thus facilitating rapid response to an SCA event, which improves the chances of survival of a SCA victim.

20 Claims, 5 Drawing Sheets

(51) Int. Cl.
| | |
|---|---|
| A61B 5/00 | (2006.01) |
| A61B 5/024 | (2006.01) |
| A61B 5/08 | (2006.01) |
| G09B 19/00 | (2006.01) |
| H04W 4/90 | (2018.01) |
| G09B 5/02 | (2006.01) |
| H04W 4/02 | (2018.01) |
| G06F 19/00 | (2018.01) |
| A61B 5/11 | (2006.01) |
| A61B 5/113 | (2006.01) |
| A61N 1/39 | (2006.01) |

(52) U.S. Cl.
CPC ............ *A61B 5/0816* (2013.01); *A61B 5/747* (2013.01); *G06F 19/00* (2013.01); *G09B 5/02* (2013.01); *G09B 19/003* (2013.01); *H04W 4/02* (2013.01); *H04W 4/90* (2018.02); *A61B 5/002* (2013.01); *A61B 5/113* (2013.01); *A61B 5/1104* (2013.01); *A61B 5/1112* (2013.01); *A61B 5/4836* (2013.01); *A61N 1/39* (2013.01)

(56) References Cited

U.S. PATENT DOCUMENTS

| | | |
|---|---|---|
| 2009/0270931 A1 | 10/2009 | Liden et al. |
| 2010/0022904 A1 | 1/2010 | Centen |
| 2012/0089054 A1 | 4/2012 | Centen et al. |
| 2014/0222462 A1* | 8/2014 | Shakil .................... G06Q 50/22 705/3 |
| 2014/0266983 A1* | 9/2014 | Christensen ......... G02B 27/017 345/8 |
| 2014/0342330 A1* | 11/2014 | Freeman .............. G09B 23/288 434/265 |
| 2015/0170546 A1* | 6/2015 | Kirenko ................ G09B 23/30 434/265 |

FOREIGN PATENT DOCUMENTS

| | | |
|---|---|---|
| WO | 2008086592 A1 | 7/2008 |
| WO | 2014186578 A1 | 11/2014 |
| WO | 2017001555 A1 | 1/2017 |

OTHER PUBLICATIONS

Jaeger et al: "First-Aid Sensor System: New Methods for Single-Point Detection and Analysis of Vital Parameters Such as Pulse and Respiration"; Proceedings of the 29th Annual International Conference of the IEEE EMBS, Lyon France, Aug. 2007, pp. 1-4.

Lippert et al: "European Resuscitation Counsil Guidelines for Resuscitation 2010 Section 10. The Ethics of Resuscitation and End-of-Life Decisions"; Resuscitation, 81, 2010, pp. 1445-1451.

Maeda et al: "Parasitic Humanoid: The Wearable Robotics as a Behavioral Assist Interface Like Oneness Between Horse and Rider"; Conference AH'11, Mar. 12-14 Tokyo, Japan, 2011.

Boulden: "Physician Advocates Medical Innovation With Google Glass"; (cited as Trimble in specification),UAMS News, Jul. 24, 2013, 2 Page Document.

* cited by examiner

CARDIOPULMONARY RESUSCITATION GUIDANCE METHOD, COMPUTER PROGRAM PRODUCT AND SYSTEM

CROSS-REFERENCE TO PRIOR APPLICATIONS

This application is the U.S. National Phase application under 35 U.S.C. § 371 of International Application No. PCT/EP2016/060933, filed on May 16, 2016, which claims the benefit of European Patent Application No. 15169581.4, filed on May 28, 2015 and European Patent Application No. 15174415.8, filed Jun. 30, 2015. These applications are hereby incorporated by reference herein.

FIELD OF THE INVENTION

The present invention relates to a cardiopulmonary resuscitation guidance method.

The present invention further relates to a computer program product for implementing such a cardiopulmonary resuscitation guidance method.

The present invention yet further relates to a cardiopulmonary resuscitation guidance system for executing the computer program product.

BACKGROUND OF THE INVENTION

Worldwide a large number of people suffer sudden cardiac arrest (SCA) events. For instance, in Europe alone there are between 350,000 and 700,000 out of hospital sudden cardiac arrest (SCA) events every year which are frequently witnessed by (untrained) lay people. Cardiopulmonary resuscitation (CPR) is the key life-saving intervention recommended by international guidelines for victims of SCA, where necessary (in about ⅓ of all SCA cases) supplemented by defibrillation using an automatic external defibrillator (AED). CPR involves the delivery of chest compressions (CCs) at a depth of at least 5 cm and at a rate of 100 compressions per minute (cpm), in combination with artificial ventilation (i.e., rescue breaths) to maintain the circulatory flow and oxygen supply to the vital organs in the body of the SCA sufferer until spontaneous circulation returns.

For successful resuscitation it is essential that CPR is performed as soon as possible. Currently, international guidelines recommend that the cardiac arrest situation is recognised within 5-10 sec following the SCA event by performing a breathing check. Prior to 2005, a manual pulse check in addition to the breathing check was recommended by the guidelines for the diagnosis of cardiac arrest. This recommendation was removed from the CPR guidelines due to the unwillingness and the inability of lay rescuers to quickly and correctly perform pulse palpation. Nevertheless, pulse detection is still perceived by the resuscitation community as an important (supplementary) technique for the assessment of the need for CPR in an emergency situation.

With every minute that passes prior to initiating CPR, the probability of saving a victim's life decreases by 10% and after 10 minutes there is almost no chance of successful resuscitation. Moreover, poor CC performance, i.e., insufficient depth, rate and/or duration of CC by lay rescuers is one of the main factors contributing to the reported low post-CPR survival rate for victims of out-of-hospital cardiac arrests, which is between 9.5% and 11.4%.

In addition, challenging terrain (e.g., bush, ice, soft snow, sloping, rocky or uneven ground, etc.), harsh environmental conditions (e.g., snow, mist, fog, rain, low lighting) and safety hazards (e.g., chemical spills, downed power lines, fire, smoke, vehicle traffic, etc.) present significant barriers to the delivery of effective CPR, and may partly contribute to the reported low post-CPR survival rate. For example, performing chest compressions during CPR on an inclined or soft back support surface will produce shallower, less effective compressions, which will lead to poorer survival outcomes. Moreover, current CPR guidelines recommend that prior to initiation of CPR lay rescuers should always check for any potential hazards and should only approach the victim after determining that the scene is safe. This is especially important since many people may act impulsively and place themselves in harm's way, due to difficulties in thinking clearly as a result of the highly stressful emergency situation.

Hence there is a profound need for a solution that can assist lay rescuers in the management of the CPR workflow of bystander lay rescuers and can provide CC guidance to enable them to deliver effective CPR in a timely manner.

Many commercial solutions exist for CPR workflow management and CC guidance during CPR; however, these solutions are primarily aimed at meeting the needs of professional, Basic Life Support (BLS) and Advanced Life Support (ALS) users. In recent times some solutions aimed at lay rescuers have become available or are currently under development.

For example, EP 2 308 450 A1 discloses an apparatus for assisting a rescuer in performing chest compressions during CPR on a victim, the apparatus comprising a pad or other structure configured to be applied to the chest near or at the location at which the rescuer applies force to produce the chest compressions, at least one sensor connected to the pad, the sensor being configured to sense movement of the chest or force applied to the chest, processing circuitry for processing the output of the sensor to determine whether the rescuer is substantially releasing the chest following chest compressions, and at least one prompting element connected to the processing circuitry for providing the rescuer with information as to whether the chest is being substantially released following chest compressions. In particular, the apparatus comprises a bistable mechanical element providing tactile and optionally audible feedback to the rescuer, thereby indicating the beginning and the end of a compression cycle. A drawback of this apparatus is that the feedback provided by the apparatus may be difficult to interpret by a lay rescuer, such that the feedback may not lead to an improvement of the CPR being administered, thus reducing the survival risk of the victim.

US 2008/0171311 A1 discloses a CPR assist glove adapted to provide CPR guidance. The glove contains an accelerometer, a plurality of pressure sensors and an ECG sensor all coupled to a processing unit for processing the sensed parameters and for providing CPR guidance based on the processed parameters to a feedback device such as a display device on the glove or a separate display device of a computer or the like. This however is not ideal. The size of the glove limits the dimensions of the display device that can be incorporated therein, such that the rescuer may struggle to read the guidance on the display device when the hand of the rescuer is placed on the chest of the victim. On the other hand, a separate display device may be bigger but forces the rescuer to look away from the victim, thus hampering the CPR workflow. Moreover, the number of lay rescuers that will routinely carry such a dedicated CPR assist glove is likely to be rather limited.

US 2014/342330 A1 discloses a device for assisting rescuers in performing CPR and a method for managing CPR treatment to a person in need of emergency assistance, which includes capturing one or more images at a scene where the person in need of medical assistance is being treated using one or more cameras at the scene, performing automatic computer-based analysis of the images to identify a quality of treatment provided to the person in need of medical assistance, and using analysis of the images to direct rescuers at the scene of the person in need of medical assistance in performing care for the person in need of medical assistance.

Internet publication "Education & Research Feature—Physician Advocates Medical Innovation with Google Glass", by Christina Trimble, University of Arkansas for Medical Sciences, Jul. 24, 2013, proposes the use of Google glass to assist individuals in performing CPR on a victim of cardiac arrest.

In addition, recently there has been a proliferation of smart device applications for lay rescuer CPR guidance, e.g., the Pocket First Aid & CPR, the Real time CPR guide and the CPR metronome, which can be obtained in app stores around the world, e.g. the Google Play Store. However, these apps are primarily for training and are unsuitable for real-time CPR guidance because they require continuous user input and interaction, again hampering CPR workflow.

SUMMARY OF THE INVENTION

The present invention seeks to provide a CPR guidance method that overcomes at least some of these drawbacks.

The present invention further seeks to provide a computer program product comprising a computer-readable medium embodying computer program code for implementing this method.

The present invention yet further seeks to provide a CPR guidance system for executing this computer program code.

According to an aspect, there is provided a cardiopulmonary resuscitation (CPR) guidance method for a system including a head-mountable computing device comprising a processor and at least one display module arranged to be viewed by the wearer of the head-mountable computing device when wearing the device, the method comprising receiving, on said processor, a first signal conveying vital signs information from at least one sensor for monitoring vital signs of a patient, wherein a sensor of the at least one sensor is integrated in the head-mountable computing device; processing said first signal on said processor to extract the vital signs information; and displaying cardiopulmonary resuscitation guidance on said at least one display module in response to the processed vital signs information. The provision of CPR guidance on the at least one display module of the head-mountable computing device ensures that the rescuer is presented with clearly legible CPR guidance without having to look away from the victim to be treated. Moreover, as there is a clear trend in society towards smart wearable devices, it is reasonable to assume that a significant number of lay persons will be in the possession of such a head-mountable computing device, thereby increasing the likelihood of a SCA sufferer being provided with life-saving CPR, i.e. CPR that is administered correctly due to the guidance provided by the method of the present invention.

The vital signs information may comprise at least one of breathing information and pulse information, for instance to assess if CPR should be initiated and/or to assess if CPR may be terminated in case of the return of a spontaneous pulse and/or breathing rhythm of the victim.

Preferably, the method further comprises receiving, on said processor, patient chest compression characteristics from a further sensor for detecting said patient chest compression characteristics; processing said chest compression characteristics on said processor; and displaying adjusted cardiopulmonary resuscitation guidance in response to the processed patient chest compression characteristics. In this manner, the lay rescuer may be trained on the spot in how to correctly administer chest compressions, for instance when the further sensor detects that chest compressions of incorrect depth and/or frequency are being provided, in which case the processor may be adapted to provide the lay rescuer with instructions on how to correctly perform chest compressions.

In an embodiment, displaying adjusted cardiopulmonary resuscitation guidance comprises displaying a suggested change of administrator of the cardiopulmonary resuscitation in response to a gradual decline in at least one of chest compression depth and chest compression frequency. This ensures that during prolonged CPR administration fatigue of the rescuer can be addressed by changing rescuers, thereby avoiding the risk of fatigue-induced substandard CPR administration.

In some embodiments, the method further comprises receiving, at said processor, a second signal conveying environmental information from at least one sensor for sensing an environment within which the patient is located; processing second signal on said processor to extract the environmental information; and displaying adjusted cardiopulmonary resuscitation guidance on said at least one display module in response to the processed environmental information. The provision of CPR guidance to a user based on information about an environment within which the patient is located may assist lay rescuers in the assessment and management of hazards and challenging conditions during an SCA event or other emergency situation to enable them to deliver effective CPR in a timely manner. The CPR guidance may take account of a surrounding environment during an SCA event or an emergency situation, thereby enabling a lay rescuer to take appropriate action in view of environmental conditions, hazards and terrain challenges.

Some of these embodiments may provide CPR guidance that accounts for conditions which may adversely influence the delivery of effective CPR, e.g., inclined or uneven terrain, soft/unstable ground (e.g., snow, ice) or low lighting conditions. Furthermore, some of these embodiments may be portable and suitable for ubiquitous access during an SCA event or semergency situation.

The environmental information may comprise at least one of: location information; traffic information; weather information; and hazard information, for instance to assess if preliminary or preparatory action should be undertaken and/or to assess if CPR should be initiated. Also, the environmental information may enable the assessment and identification of environmental conditions and terrain challenges which could adversely affect the delivery of effective CPR. Some of these embodiments may therefore provide CPR guidance which takes account of a context of an SCA event or emergency situation.

The environmental information may, for example, be processed to assess and identify hazards in the vicinity of an SCA or accident victim which may pose a threat to the safety of the lay rescuer or the victim. By way of example, hazards or threats (such as fire, smoke, vehicle traffic, gas or chemical leaks, downed power lines or live electrical items, falling objects, etc.) in the vicinity of the SCA or accident victim may be identified using a camera and microphone directed towards the victim/patient. Hazard and threat identification may then be accomplished via image and sound classification algorithms incorporating face, object and sound recognition. This processing may be done on the 'Cloud' (e.g. via a distributed processing environment).

Additionally environmental information may be provided by other sources or services. For example, traffic information, local weather conditions, location specific hazards from a database can be used.

Preferably, the step of displaying adjusted cardiopulmonary resuscitation guidance may comprise: displaying a suggested change of location of the patient in response to the processed environmental information. For example, if hazards are detected or inferred, the user may be advised of the potential threats and guided via visual and/or voice prompts to mitigate the risk posed by the hazards by moving the patient (e.g. if there is a fire nearby or a pool of water near the patient which may cause electrocution during an AED shock). The user (e.g. a lay rescuer) may even be advised that the situation is too dangerous to permit intervention. In such an instance, the user may be further guided to a safe nearby location to await emergency services arrival (e.g. using location information obtained by a GPS tracker of the system).

In some of these embodiments, displaying adjusted cardiopulmonary resuscitation guidance may comprise displaying a suggested change of position of the patient in response to the breathing information indicating that the patient is breathing. For example, if the patient is breathing, the user may be instructed via visual and/or voice prompts to place the patient in the recovery position and then await the arrival of emergency services.

In some of these embodiments, displaying adjusted cardiopulmonary resuscitation guidance may comprise: displaying a suggested change of location of the patient in response to the breathing information indicating that the patient is not breathing and further based the processed environmental information. For example, if the patient is not breathing, the environmental conditions and terrain where the patient is located may be assessed using images from a camera and image processing algorithms to assess the lighting conditions, the inclination of the ground and suitability of the ground surface for compression during CPR. Alternatively, this can be accomplished by placing a sensor or portable computing device (e.g., smartphone or smartwatch) directly on the patient's chest and then using signals from a built-in accelerometer to assess the inclination or unevenness of the ground and a motion classification algorithm to assess the instability and softness of the ground surface. If it is determined that the patient is located in an area where the environmental conditions and/or terrain are unsuitable for the performance of effective CPR, e.g., if there is ice, mist, snow, poor light, or an inclined, unstable or uneven ground surface, etc., then a GPS tracker of the head-mountable computing device may be used to guide the lay rescuer, via audio and visual prompts, to a nearby safe location which is suitable for CPR. The adjusted cardiopulmonary resuscitation guidance may then advise the user to initiate and continue CPR until the arrival of emergency services.

In a particularly advantageous embodiment, the method further comprises automatically identifying devices for wirelessly communicating with the head-mountable computing device, wherein each of said devices comprise at least one of a sensor for monitoring vital signs of a patient, a sensor for sensing the environment within which a patient/victim is located, and a further sensor for detecting at least one of patient chest compression characteristics and breathing characteristics; and wirelessly connecting selected identified devices to the head-mountable computing device. This embodiment utilizes the insight that the rescuer or bystanders may carry (smart) devices that are capable of performing vital signs sensing and/or chest compression characteristics sensing, such that the CPR guidance system may be compiled in situ by integrating devices in the vicinity of the rescuer into the CPR guidance system, e.g. in an automated or user-controller manner.

The method may further comprise generating an alert on the at least one display module for alerting a wearer of the head-mountable computing device to enable a wireless communication mode of an identified device. In this manner, devices having the desired sensing capability can be manually configured such that they can be included into the CPR guidance system.

The method may further comprise displaying positioning information for positioning the selected identified devices on the patient/victim on the at least one display module in order to ensure that the devices added to the CPR guidance system are correctly positioned on the victim.

In an embodiment, the method further comprises automatically identifying a defibrillator device in the vicinity of the patient/victim; and providing user instructions for said defibrillator device on the at least one display device. By detecting such a defibrillator device, defibrillation can be added to the CPR workflow, thus further improving the survival changes of the victim especially when defibrillation significantly improves such survival chances.

In a further embodiment, the method further comprises automatically connecting to a remote emergency service with said system; and sending a distress signal to said service with said system, said signal including environmental information such as location information (e.g. global positioning information). This ensures that the victim will receive professional medical help as soon as possible.

According to another aspect, there is provided a computer-readable medium embodying computer program code for implementing the method of any of the above embodiments when executed on a processor of a head-mountable computing device further comprising at least one display module arranged to be viewed by the wearer of the head-mountable computing device when wearing the device. Such a computer program product, when executed on a CPR guidance system of the present invention, facilitates the administration of particularly effective CPR as explained in more detail above.

According to yet another aspect, there is provided a cardiopulmonary resuscitation (CPR) guidance system including the above computer program product and a head-mountable computing device comprising a sensor for monitoring vital signs of a patient (10), at least one display module arranged to be viewed by the wearer of the head-mountable computing device when wearing the device, and a processor adapted to execute the computer program code of said computer program product. Such a CPR guidance system facilitates a rescuer to be presented with CPR guidance, and that may optionally assist lay rescuers in the assessment and management of hazards and challenging conditions during an SCA event or other emergency situation to enable them to deliver effective CPR in a timely manner, whilst allowing the rescuer to focus on the victim to be treated, whilst furthermore allowing the use of external devices as sensors of the CPR guidance system as explained above.

The CPR guidance system may further comprise one or more of the at least one sensor for monitoring vital signs of a patient that is external to the head-mountable computing device.

The CPR guidance system may further comprise the further sensor.

The CPR guidance system may be a modular system wherein the head-mountable computing device, one or more of the at least one sensor that is external to the head-mountable computing device and/or the further sensor are separate modules, e.g. separate devices in communication with each other, e.g. wireless communication.

For example, the further sensor may be integrated in a portable or wearable device such as a smart phone or smart watch. This has the advantage that ubiquitous devices can be combined, e.g. in situ, to form the CPR guidance system of the present invention, thus increasing the chances of such a CPR guidance system being available in the event of an out of hospital SCA event.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
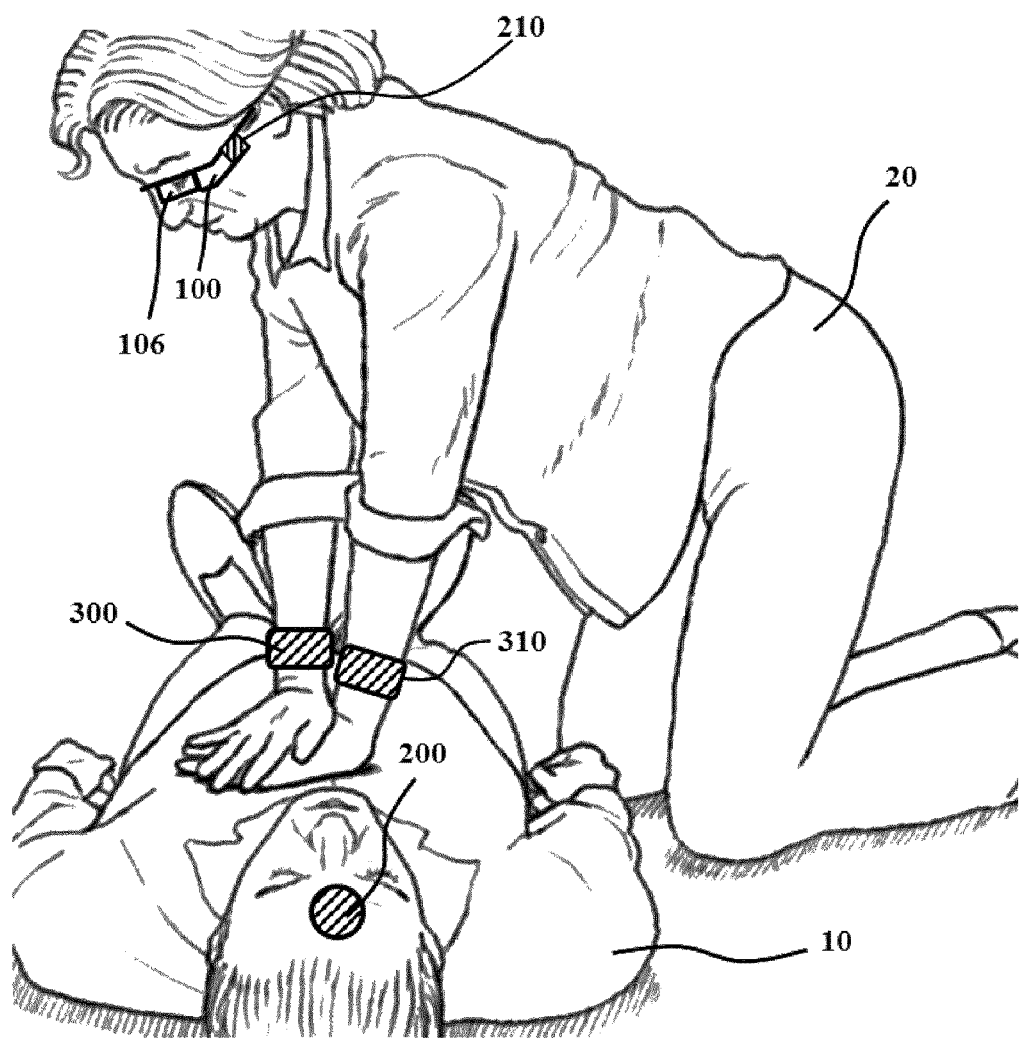
FIG. 1 schematically depicts an embodiment of a CPR guidance system of the invention.

It should be understood that the Figures are merely schematic and are not drawn to scale. It should also be understood that the same reference numerals are used throughout the Figures to indicate the same or similar parts.

In the context of the present application, a head-mountable computing device is a device that can be worn of the head of its user and provides the user with computing functionality. The head-mountable computing device may be configured to perform specific computing tasks as specified in a software application (app) that may be retrieved from the Internet or another computer-readable medium. Non-limiting examples of such head-mountable computing devices include smart headgear, e.g. eyeglasses, goggles, a helmet, a hat, a visor, a headband, or any other device that can be supported on or from the wearer's head, and so on.

FIG. 1 schematically depicts a rescuer 20 applying CPR to a victim or patient 10 using a CPR guidance system according to an embodiment of the present invention. The CPR guidance system typically comprises a head-mountable computing device 100 to be worn by the rescuer 20, which provides the rescuer 20 with CPR guidance in the form of displayed instructions on a display module 106 of the head-mountable computing device 100. By way of non-limiting example, the head-mountable computing device 100 is depicted as smart glasses, but it should be understood that the head-mountable computing device 100 may take any suitable shape as previously explained. The head-mountable computing device 100 typically comprises at least one display module 106, which may be a see-through or transparent display module 106.

Figure 2:
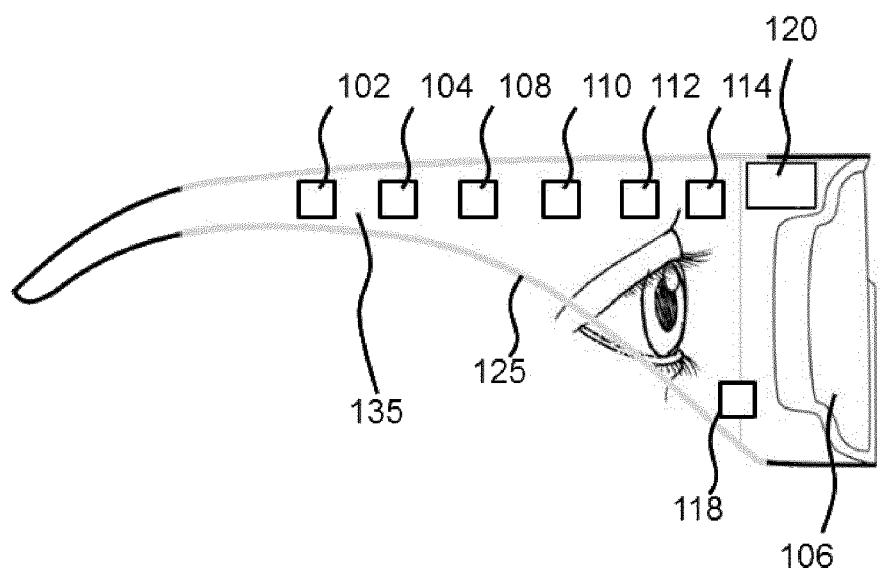
FIG. 2 schematically depicts an aspect of the CPR guidance system of FIG. 1 in more detail.

FIG. 2 schematically depicts an example embodiment of such a head-mountable computing device 100 in more detail. In some embodiments, the head-mountable computing device 100 may be adapted to wirelessly communicate with remote components of the CPR guidance system, as will be explained in more detail below. To this end, the head-mountable computing device 100 may include a wireless communication interface 102 for wirelessly communicating with such a remote target. Any suitable wireless communication protocol may be used for any of the wireless communication between the head-mountable computing device 100 and such remote components, e.g., an infrared link, Zigbee, Bluetooth, a wireless local area network protocol such as in accordance with the IEEE 802.11 standards, a 2G, 3G or 4G telecommunication protocol, and so on.

The head-mountable computing device 100 may optionally comprise a further wireless communication interface 104 for wirelessly communicating with a further remote system, e.g. a wireless LAN, through which the head-mountable computing device 100 may access a remote data source such as the Internet, for instance to retrieve data from a remote database as will be explained in more detail below. Alternatively, the head-mountable computing device 100 may include one wireless communication interface that is able to communicate with various remote targets. The data processor 110 may further be adapted to control wireless communication interface 102 and, if present, wireless communication interface 104.

The at least one display module 106 may be under control of a discrete display processor 108, which discrete display processor 108 may be controlled by the data processor 110, for instance receive instructions from the data processor 110 for displaying CPR guidance on the at least one display module 106. Alternatively, the display processor 108 and the data processor 110 may be implemented by a single processor, e.g. a general purpose processor or an application specific integrated circuit (ASIC).

In some embodiments, the head-mountable computing device 100 may be arranged to detect a user instruction and to trigger an operation in response to the detected user instruction, e.g. using at least one further sensor 118 including a motion sensor like a gyroscope or similar in case the user instruction is a head motion, or by including an outward-facing image sensor or camera to capture an image of a gesture-based instruction made by the wearer. Other suitable sensors for such gesture or motion capturing will be apparent to the skilled person.

The data processor 110 may be arranged to recognize a gesture or motion made by its wearer from the captured sensor data and to interpret the recognized gesture or motion as an instruction. Non-limiting examples of such a motion for instance include a turn or nod of the wearer's head. Non-limiting examples of such a gesture for instance include a hand or finger gesture in the field of view through the head-mountable computing device 100, which may be detected in an image captured with an outward facing image sensor 120.

Alternatively or additionally, the at least one further sensor 118 may include a sound sensor, e.g. a microphone, may be present to detect a spoken instruction, wherein the processor 110 may be communicatively coupled to the further sensor in order to process the sensor data and detect the spoken instruction.

The at least one further sensor 118 may additionally or alternatively include an input sensor, e.g. a button or the like for facilitating the wearer of the head-mountable computing device 100 to select a user instruction from a list of options. Such list of options for instance may be displayed on a display module 106 of the head-mountable computing device 100. Such an input sensor may form part of a user interface for receiving input from the user. Such a user interface may include, for example, a touchpad, a keypad, buttons, a microphone, and/or other input devices. The data processor 110 may control at least some of the functioning of head-mountable computing device 100 based on input received through the user interface. In some embodiments, any of the at least one further sensors 118 may define or form part of the user interface.

In some embodiments, the head-mountable computing device 100 may further comprise an audio output device 114 such as a loudspeaker or the like for providing the wearer of the head-mountable computing device 100 with audio instructions, e.g. spoken instructions supplementary to the CPR guidance to be displayed on the at least one display module 106. Any suitable audio output device may be used for this purpose.

The head-mountable computing device 100 may further comprise a data storage device 112, e.g. for storing the CPR guidance data to be displayed. Any suitable type of data storage may be used, e.g. non-volatile or flash memory, PROM, EEPROM and so on.

The various components of the head-mountable computing device 100 may be integrated in the device in any suitable manner, such as integrated in a part 135 of a mounting frame of the head-mountable computing device 100 by way of non-limiting example. FIG. 2 schematically depicts an example embodiment of the head-mountable computing device 100 in which the device comprises a single display module 106 only, which single display module 106 may be arranged to be observable by a single eye of the wearer of the head-mountable computing device 100. It should be understood that this is by way of non-limiting example only, and that it is equally feasible to provide a head-mountable computing device 100 in which prospective display modules 106 are provided for each eye of the rescuer 20. The at least one display module 106 is typically arranged such that a wearer of the head-mountable computing device 100, i.e. the rescuer, can observe an image displayed on the at least one the display module 106. Preferably, the at least one display module 106 is a see-through or transparent display module such that the wearer can observe at least a part of a field of view through the display module 106, such that the wearer can wear the head-mountable computing device 100 whilst performing CPR on the victim 10.

The at least one display module 106 may be provided in any suitable form, such as a transparent lens portion. Alternatively, the head-mountable computing device 100 may comprise a pair of such a lens portions, i.e. one for each eye as explained above. The one or more transparent lens portions may be dimensioned such that substantially the entire field of view of the wearer is obtained through the one or more transparent lens portions. For instance, the at least one display module 106 may be shaped as a lens to be mounted in a frame 125 of the head-mountable computing device 100. It will be understood that the frame 125 may have any suitable shape and may be made of any suitable material, e.g. a metal, metal alloy, plastics material or combination thereof. Several components of the head-mountable computing device 100 may be mounted in the frame 125, such as in a component housing 135 forming part of the frame 125. The component housing 135 may have any suitable shape, preferably an ergonomic shape that allows the head-mountable computing device 100 to be worn by its wearer in a comfortable manner.

As also shown in FIG. 1, the CPR guidance system further comprises a sensor 200 external to the head-mountable computing device 100 for detecting vital signs of the victim 10, such as breathing and/or a pulse. In addition the CPR guidance system comprises a sensor 210 integrated in the head-mountable computing device 100 also for detecting vital signs of the victim 10. For example, head-mountable computing device 100 may comprise a forward facing camera 120 for capturing an image of (the face of) the victim 10, which image (or sequence of images) may be processed by the data processor 110 in order to extract vital signs information from the image (or sequence of images), e.g. using an application from the memory 112 for extracting vital signs information from a captured image, as is well-known per se. Alternatively, one or more sensors 200 external to the head-mountable computing device 100 may be used in combination with a sensor 210 integrated in the head-mountable computing device 100. Such external sensors may be dedicated sensor devices that the rescuer 20 may carry around or may be vital signs sensors incorporated in a smart device such as a smart watch or a smart phone. For example, such an external sensor may be enclosed within the smart device and may be exposed by removal of a cover or the like of the smart device such that the external sensor 200 can be attached to the victim 10. A surface of the external sensor 200 may comprise an adhesive layer to aid such attachment. Attachment instructions may be displayed on the at least one display module 106 of the head-mountable computing device 100 as will be explained in more detail below.

In an embodiment, multiple vital signs sensors 200 external to the head-mountable computing device 100 may be placed on different parts of the body of the victim, e.g. on the forehead of the victim, on an artery in the neck of the victim, and so on, to allow for accurate monitoring of the vital signs of the victim 10. In the context of the present application, vital signs include at least one of a breathing pattern or rhythm and a pulse rhythm. It should be understood for the avoidance of doubt that a pulse rhythm is not necessarily detected in the pulse of a victim 10, but may be detected at any suitable part of the body of the victim 10 as is well-known per se. Where a vital signs sensor 200 is external to the head-mountable device 100, the vital signs sensor 200 preferably is connected to the head-mountable device 100 in a wireless fashion using one of the wireless interfaces 102 or 104, using any suitable wireless protocol as previously explained. As will be explained in more detail below, the data captured by the one or more sensors 200 is typically processed by the data processor 110, which processed data is used to generate and display CPR guidance on the at least one display module 106, thereby providing the rescuer 20 with guidance on how to administer CPR.

In an embodiment, the CPR guidance system further comprises a further sensor 300 for monitoring chest compression characteristics, i.e. data relating to the quality of the chest compressions administered by the rescuer 20 to the victim 10. Such a further sensor 300 for instance may comprise a motion sensor such as a gyroscope or accelerometer to determine parameters such as the depth of the compressions administered by the rescuer 20, i.e. the displacement distance normal to the chest of the victim 10, and the frequency of the compressions. In an embodiment, the further sensor 300 may be integrated in the head-mountable computing device 100. However, in order to obtain a more direct correlation between the data collected by the further sensor 300 and the chest compressions administered by the rescuer 20, it is preferable that the further sensor 300 is external to the head-mountable computing device 100.

The further sensor 300 may be worn by the rescuer 20 as shown in FIG. 1. For example, the further sensor 300 may be integrated in a device worn on the wrist of the rescuer 20, such as a smart watch or the like, or may be integrated in the device worn on the hand of the rescuer 20, such as a glove including the further sensor 300. By wearing the further sensor 300 in close proximity to the hand of the rescuer 20, the hand motion resulting from the administration of the chest compressions can be accurately captured by the further sensor 300. As before, where the further sensor 300 is external to the head-mountable computing device 100, the further sensor 300 preferably is connected to the head-mountable device 100 in a wireless fashion using one of the wireless interfaces 102 or 104, using any suitable wireless protocol as previously explained. As will be explained in more detail below, the data captured by the further sensor 300 is typically processed by the data processor 110, which processed data is used to check if the rescuer 20 administers the chest compressions in a correct fashion, i.e. by compressing the chest of the victim 10 to a sufficient depth and/or by applying chest compressions is an appropriate frequency, e.g. about 100 chest compressions per minute. In case the data processor 110 determines that the chest compressions are not administered correctly by the rescuer 20, of the data processor 110 may trigger the display of chest compression guidance information on the at least one display module 106, thereby providing the rescuer 20 with guidance on how to correctly and administer chest compressions or providing the rescuer 20 with instructions to hand over the task of administering CPR to another rescuer, for instance because the data processor 110 has detected a gradual decline in the quality of the administered chest compressions, which may indicate fatigue of the rescuer 20.

Figure 3:
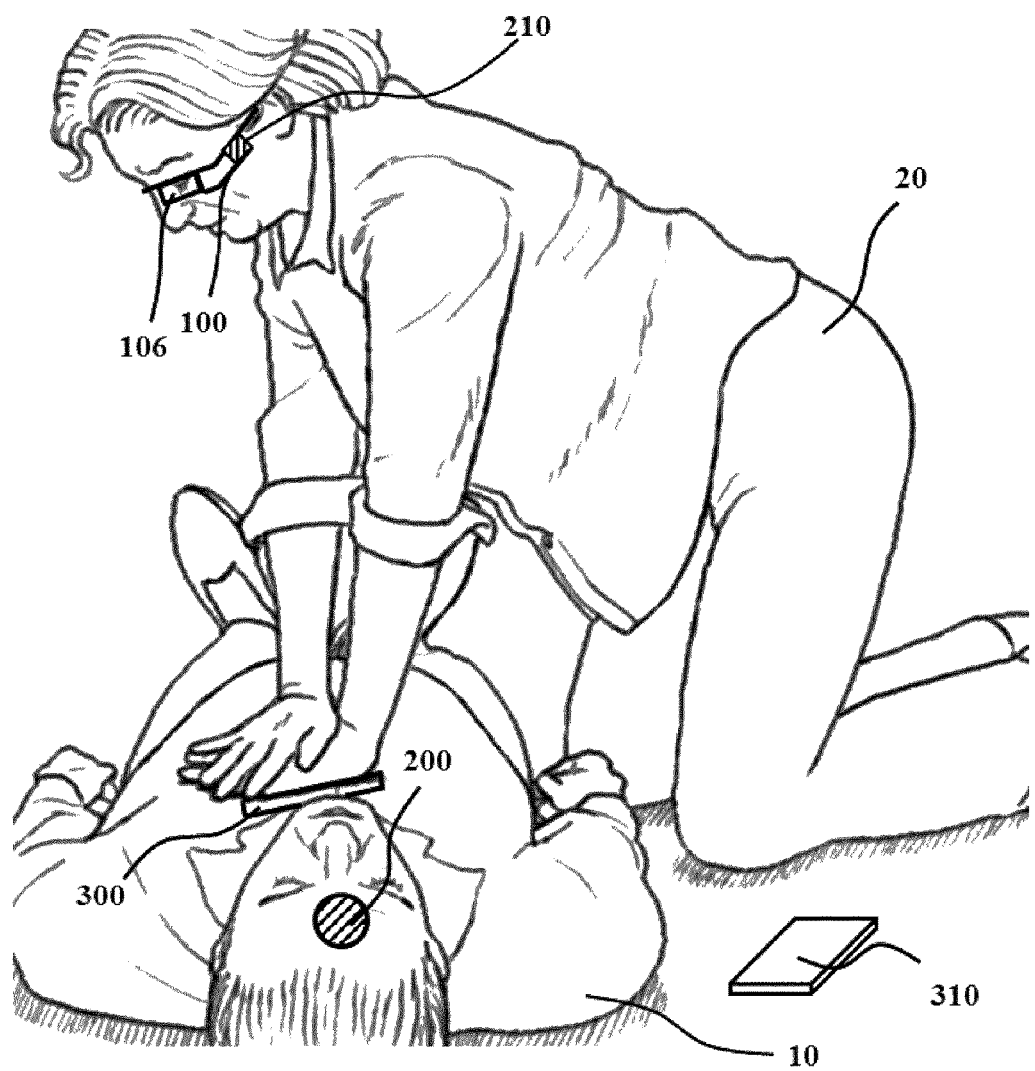
FIG. 3 schematically depicts another embodiment of a CPR guidance system of the invention.

It is not necessary for the further sensor 300 to be worn by the rescuer 20. FIG. 3 schematically depicts an alternative embodiment of the further sensor 300, wherein the further sensor 300 is placed in between the hands of the rescuer 20 and the chest of the victim 10, such that chest compressions are applied to the victim 10 through the further sensor 300. As before, the further sensor 300 may be integrated in a smart device, e.g. a smart wearable device such as a smart watch, wherein the smart watch may be removed from the wrist of the rescuer 20 or from the wrist of a bystander providing the further sensor 300 as will be explained in more detail below, or a smart non-wearable device such as a smart phone, which may be provided by the rescuer 20 or a bystander as will be explained in more detail below.

In an embodiment, the CPR guidance system further comprises a sensor 310 for sensing an environment within which a victim is located, i.e. data relating to characteristics and/or attributes of the surrounding environment of the rescuer 20 or the victim 10. Such a sensor 310 for sensing an environment may for instance comprise a global positioning system (GPS) unit for determining the location of the rescuer 20, i.e. the location of the sensor 310.

As will be explained in more detail below, the data captured by the sensor 310 for sensing an environment is typically processed by the data processor 110, which processed data is used to take account of a surrounding environment during an SCA event or an emergency situation, thereby enabling a lay rescuer to take appropriate action in view of environmental conditions, hazards and terrain challenges.

In case the data processor 110 determines that the environment within which a victim is located is comprises environmental conditions, hazards and/or terrain challenges, the data processor 110 may trigger the display of guidance information on the at least one display module 106, thereby providing the rescuer 20 with guidance on how to take appropriate action in view of environmental conditions, hazards and terrain challenges.

For example, hazards or threats (such as fire, smoke, vehicle traffic, gas or chemical leaks, downed power lines or live electrical items, falling objects, etc.) in the vicinity of the sensor 310 may be identified using location information from the sensor 310. The location information may, for example, may be processed in conjunction with traffic information, weather information, location specific hazards, etc. from a database.

Additionally and/or alternatively, environmental information may be obtained using a camera and microphone integrated in the head-mountable computing device 100. Hazard and threat identification may then be accomplished via image and sound classification algorithms incorporating face, object and sound recognition. This processing may be done on the 'Cloud' (e.g. via a distributed processing environment).

Additionally, or alternatively, environmental information may be provided by other sources or services.

In case the data processor 110 determines that the environment within which a patient/victim is located is comprises environmental conditions, hazards and/or terrain challenges that prevent the safe administration of CPR, the data processor 110 may trigger the communication of guidance information advising the rescuer 20 of the potential threats and guiding, via voice or visual prompts, how to mitigate the risk posed by the hazards by moving the victim. The data processor 110 may even communicate that the situation is too dangerous to permit intervention. In such an instance, the rescuer 20 may be further guided to a safe nearby location to await emergency services arrival (e.g. using location information obtained by the sensor 310).

As in the case of the further sensor 300, it is not necessary for the sensor 310 for sensing an environment to be worn by the rescuer 20. FIG. 3 schematically depicts an alternative embodiment of the sensor 310 for sensing an environment, wherein the sensor 310 is provided by a smartphone 310. For example, the sensor 310 may be integrated in a mobile phone, wherein the mobile phone may be positioned in the close vicinity of the victim 10 so as to provide yet a further sensor 310 as will be explained in more detail below.

Embodiments may be arranged to use existing sensors in one or more portable computing devices (such as a smart watch, smartphone or other wearable sensor platform), to aid lay rescuers in the assessment of environmental conditions, hazards and terrain challenges during an SCA event or emergency situation.

Moreover, conventional and widely-available smart devices typically incorporate many different sensors which are suitable for the assessment of environmental conditions, hazards and terrain challenges. These include a GPS tracker, a sophisticated user interface (e.g., a LCD display, AMO-LED, etc.), capable of visual and audible guidance, as well as a telecommunication system which enables the alerting of emergency services. In addition, many smart devices also have additional sensors including an accelerometer, video camera and a photo-plethysmography (PPG) sensor which may be useful in the execution of the CPR workflow such as real-time feedback on the presence of vital signs. Such portable or wearable computing devices may therefore be leveraged to support a CPR guidance system, which can be used to assist lay rescuer intervention whenever or wherever an emergency situation occurs.

Thus, there may be provided a method for assessing and identify hazards in the vicinity of an SCA or accident victim which may pose a threat to the safety of the lay rescuer or the victim. Embodiments may also assess and identify environmental conditions and terrain challenges which may adversely affect the delivery of effective CPR. Using such assessment(s), a lay rescuer may be guided to mitigate or avoid hazards and/or to manage all environmental conditions and terrain challenges so as to ensure safe and effective CPR performance.

The environmental information may comprise at least one of: location information; traffic information; weather information; and hazard information, for instance to assess if preliminary or preparatory action should be undertaken and/or to assess if CPR should be initiated. Location information may, for example, comprise information relating to properties and/or characteristics of an environment or place such as absolute position, relative position, terrain characteristics, entity presence information, and the like. Weather information may, for example, comprise information relating to properties and/or characteristics of local weather conditions at an environment or place such as temperature, humidity, atmospheric pressure, wind conditions, etc. Traffic information may, for example, comprise information relating to properties and/or characteristics of traffic at an environment or place such as vehicle congestion, average vehicle speed, vehicle route locations and directions, vehicle route characteristics, traffic event or accident occurrences, etc. Hazard information may, for example, comprise information relating to properties and/or characteristics of hazards at an environment or place such as hazardous events occurrences/locations, fire presence, smoke presence, gas presence, chemical leak presence, downed power lines, live electrical items, fallen objects, flood waters, earthquake or volcanic eruption risk, etc.

As such, embodiment may help to prevent lay rescuers from being confused or overwhelmed when confronted with challenging and/or dangerous conditions. Also, lay rescuers may be guided to deliver effective CPR regardless of the environmental conditions faced.

At this point it is noted that the CPR guidance system may be created in situ, using ubiquitous smart devices that are in the possession, e.g. worn or carried by the rescuer 20 and bystanders. Given the rapid proliferation of such smart devices in everyday life, this therefore means that there is an excellent chance that such a CPR guidance system may be created in situ by identifying suitable components thereof at the scene of a SCA event and incorporating the identified components in the CPR guidance system, e.g. by establishing wireless links between the identified devices and the head-mountable computing device 100, and by placement of the identified devices on the victim 10 if necessary.

This will be explained in more detail with the aid of FIG. 4, which depicts a flowchart of an example embodiment of a method 40 for providing CPR guidance using the CPR guidance system of the present invention. In a preferred embodiment, the method 40 comprises a first branch 41 in which sensor devices in the vicinity of the rescuer 20 are detected and added to the CPR guidance system, and a second branch 42 in which the CPR guidance system is used to guide the rescuer 20 in administering the CPR to the victim 10. It is noted for the avoidance of doubt that the branch 41 may be omitted from the method 40 in case of a head-mountable computing device 100 comprising the sensor 210 for monitoring vital signs of the victim 10 and the further sensor 300 for monitoring the chest compression characteristics caused by the administration of chest compressions to the victim 10 by the rescuer 20, and in which the CPR guidance system does not comprise any sensor 200 for monitoring vital signs of the victim 10 external to the head-mountable computing device 100.

The method 40 may start in step 402 by the discovery of a suspected victim of a SCA event by the rescuer 20 wearing the head-mountable computing device 100. The rescuer 20 may activate a CPR administration mode of the head-mountable computing device 100, e.g. by providing the device 100 with a command as explained above that can be recognized by the device 100 as an instruction to activate the CPR administration mode, which may prompt the head-mountable computing device 100 to generate a first responder call to emergency services in step 404, in order to direct the emergency services to the location of the victim 10. To this end, the first responder call may be an automated call comprising global positioning information, which information may be obtained from a global positioning unit within the head-mountable device 100 or a global positioning unit in communication with the head-mountable device 100, e.g. a smart device such as a smart phone or a smart watch comprising a global positioning unit, which smart device is wirelessly linked to the head-mountable device 100. Alternatively, the first responder call is generated by the rescuer 20, e.g. by issuing an instruction to the head-mountable computing device 100 to generate the call.

Next, the method 40 progresses to step 406 in which the head-mountable computing device 100 searches for devices including a sensor 200 for detecting vital signs (such as breathing and/or pulse) of the victim, or a further sensor 300, or a sensor 310 for sensing the environment within which a victim is located, in the vicinity of the victim 10. Such devices may for instance be detected by identifying a wireless signal generated by these devices or by identifying a global positioning tracking signal, e.g. a GPS tracker signal, a GRS signal, a GLONASS signal or the like. These sensors may be incorporated in smart devices, e.g. a smart watch or a smart phone worn by the victim 10, the rescuer 20 or bystanders. The available devices may be recognized in any suitable manner, for instance by recognizing the device type and make (product number), e.g. from an interrogation of the devices in the vicinity of the rescuer 20, and comparing the identified device with a stored database of known devices with the desired sensor functionality, or by requesting the smart devices in the vicinity of the rescuer 20 to indicate which sensors are available for linking and then linking to the relevant sensors.

The rescuer 20 is subsequently guided in step 408 to position the identified devices on the appropriate parts of the body of the victim 10 by way of placement instructions displayed on the at least one display module 106. For example, the rescuer 20 may be guided to place a device including one of the sensors 200 external to the head-mountable computing device 100 in the neck or on the forehead of the victim 10 such that the vital signs, e.g. pulse and breathing patterns, of the victim 10 can be detected, and to place a device including a further sensor 300 on the chest of the victim 10 or on the hand or wrist of the rescuer 20 in order to provide the head-mountable computing device 100 with the sensor signals that will allow the CPR guidance system and in particular data processor 110 to generate CPR guidance as a function of the received sensor signals.

In step 410 the head-mountable computing device 100 attempts to establish a wireless connection using any suitable wireless communication protocol as previously explained to the identified devices to be incorporated in the CPR guidance system. In step 412 it is checked if the wireless connections between the identified devices and the head-mountable computing device 100 have been established. If for some reason some of the wireless connections have not been established, the method 40 proceeds to step 414 in which the rescuer 20 is alerted that some of the wireless connections could not be established, such that the rescuer 20 can attempt to adjust the affected devices, for instance by enabling a wireless communication mode of these devices. This may involve asking a bystander to activate the wireless communication mode in case the device has been provided by the bystander. The alert may be displayed on the at least one display module 106 of the head-mountable computing device 100. The method 40 then returns to step 412, to check if all devices have established a wireless communication link with the head-mountable computing device 100.

Once all devices are wirelessly connected to the head-mountable computing device 100, the method 40 proceeds to step 416 in which it is checked if all the devices are correctly positioned relative to the victim 10, e.g. are positioned in the correct positions on the body of the victim 10. This for instance may be checked by sampling the sensor data provided by the devices and checking if the sensor data, e.g. vital signs data, is of sufficient quality, or by using the camera 120 of the head-mountable computing device 100 to assess if the devices are correctly positioned, e.g. by processing the images captured by the camera 120 with the data processor 110 and determining if the devices identified in these images are placed in predefined locations. If it is determined that at least some of the devices are incorrectly positioned, the method proceeds to step 418 in which the rescuer 20 is presented with repositioning information for the incorrectly positioned devices. Such repositioning information for instance may be displayed on the at least one display module 106 of the head-mountable computing device 100. Once the rescuer 20 has repositioned the devices, the method 40 returns to step 416 where the positioning of the devices is checked again.

Once all devices for providing the desired sensor data are correctly positioned, the method 40 proceeds to the second branch 42 and in particular to step 420 in which the data provided by the one or more devices comprising a sensor for monitoring vital signs of the victim 10 is analyzed by the data processor 110 to determine if the victim 10 requires CPR, i.e. to determine if the victim 10 has a pulse and is breathing. For example, a breathing check may be performed over a period of at least 10 seconds in accordance with international guidelines. As mentioned before, a breathing check and/or a pulse check may be performed by the one or more sensors 200, 210, at least some of which are integrated in the head-mountable computing device 100 and/or at least some of which are attached to the victim 10. In an embodiment, the data processor 110 may apply weighting factors, e.g. signal quality indicators, to the vital signs data received from the one or more sensors 200, 210, in order to improve the reliability of the assessment performed in step 420.

In the absence of a detected pulse and/or breathing pattern, the method 40 proceeds to step 422 in which the rescuer is presented with CPR guidance on the at least one display module 406, which guidance typically includes guidance regarding the way in which chest compressions and rescue breaths should be administered, e.g. information about the chest compression depth and frequency, information about when to administer how many rescue breaths and so on.

Once the rescuer 20 has started administering the CPR to the victim 10, the method 40 proceeds to step 426 in which the quality of the chest compressions is monitored by the data processor 110 using the sensor data provided by the further sensor 300, e.g. preferably a further sensor 300 external to the head-mountable computing device 100 placed on the chest of the victim 10 or worn on the hand or wrist of the rescuer 20, e.g. a further sensor 300 integrated in smart device such as a smart watch, a sensing glove or a smart phone, as explained in more detail above. If it is determined in step 426 that the chest compressions are correctly administered, the method 40 returns to step 420 in which it is checked if the victim 10 is breathing independently and/or has regained a pulse. If this is not the case, the method refers back to step 424 (optionally skipping step 422 if the CPR instructions are still displayed on the at least one display module 106 or no longer require to be displayed).

If it is determined in step 424 that the chest compressions are not administered correctly by the rescuer 20, for instance because the chest compressions are applied at insufficient depth and/or are applied at the incorrect frequency, e.g. a frequency that is (well) below the recommended frequency of about 100 compressions per minute, the method proceeds to step 426 in which it is checked if the quality of the chest compressions has been gradually declining. If this is the case, this is an indication of the rescuer 20 having the knowledge to correctly apply chest compressions but no longer being physically able to comply with the required chest compression regime, typically because of fatigue.

If this is the case, the method 40 proceeds to step 430 in which a message is displayed on the at least one display module 106 informing the rescuer 20 that the CPR administration should be taken over by another rescuer, e.g. a bystander at the SCA event. Such a bystander for instance may be identified by the head-mountable computing device 100 contacting a remote database, e.g. a cloud database, where a device identified in step 406 may be associated with a particular owner, which owner may be classified in terms of capability to administer CPR. The rescuer 20 may be presented with the identity or location of owners capable of administering CPR such that the rescuer 20 can approach such an owner for taking over the CPR duties. Alternatively, the rescuer 20 of course can simply ask the bystanders for a volunteer to take over such CPR duties, after which the method 40 may revert back to step 420. In particular, the new rescuer may also take over the head-mountable computing device 100 from the fatigued rescuer 20, in which case the new rescuer may be presented with the CPR instructions in step 422 as previously explained prior to the new rescuer resuming CPR.

If it is determined in step 426 that the non-compliance with the required chest compression administration regime is not caused by fatigue of the rescuer 20, the method 40 proceeds to step 428 in which the rescuer 20 may be presented with more detailed chest compression technique guidance, e.g. by displaying such guidance on the at least one display module 106 of the head-mountable computing device 100 in order to allow the rescuer 20 to improve his or her chest compression technique. Upon the rescuer 20 being presented with such guidance, the method 40 may revert back to step 424 to check if the rescuer 20 now applies the correct chest compression technique.

In this manner, the method 40 will continue until the victim 10 exhibits a return to spontaneous circulation, e.g. exhibits spontaneous breathing and a pulse as detected in step 420, or until emergency services arrive on the scene to take over, upon which the method 40 may terminate in step 432 by the rescuer 20 terminating CPR and placing the victim 10 in the recovery position. This may include presenting information on how to place the victim 10 in the recovery position on the at least one display module 106 of the head-mountable computing device 100. In an embodiment, the method 40 is continued until the emergency services arrive at the scene. This may for instance include continuing to monitor the vital signs of the victim 10 even after placing the victim 10 in the recovery position, for instance to detect another SCA event.

At this point, it is noted that the above described embodiment of the method 40 is merely an example embodiment of this method and that several extensions thereto and/or variations thereon will be immediately apparent to the skilled person.

For example, the method 40 may be extended by the detection of a portable defibrillation device in the vicinity of the victim 10, e.g. in the procession of one of the bystanders, which detection for instance may take place in step 406 of the method 40 by way of non-limiting example, in which case the CPR administration module 42 may be extended by including instructions for the rescuer 20 on how to use the defibrillation device in the CPR workflow. For instance, user instructions for using the defibrillation device may be directly transferred from the defibrillation device to the head-mountable computing device 100 for displaying on the at least one display module 106.

The method 40 for instance may also be extended by the identification of the CPR competences of the bystanders in step 406 for instance, by upon identification of a smart device in the vicinity of the rescuer 20, contacting a remote database in which the smart device is registered, which database further comprises information about the owner of the smart device including information about the CPR administering abilities of the owner. In this manner, the bystanders may be divided in a first pool of CPR capable bystanders and a second pool of CPR incapable bystanders, wherein the bystanders get assigned specific tasks based on their (in)ability to administer CPR. Such tasks for instance may include crowd control, contacting the emergency services, retrieving a portable defibrillator, and so on. Such tasks may be communicated to the devices of these owners by the head-mountable computing device 100 in case the data processor 110 assigns these tasks to these owners, or may be communicated to these owners by a remote control center for instance associated with the remote database.

Figure 4:
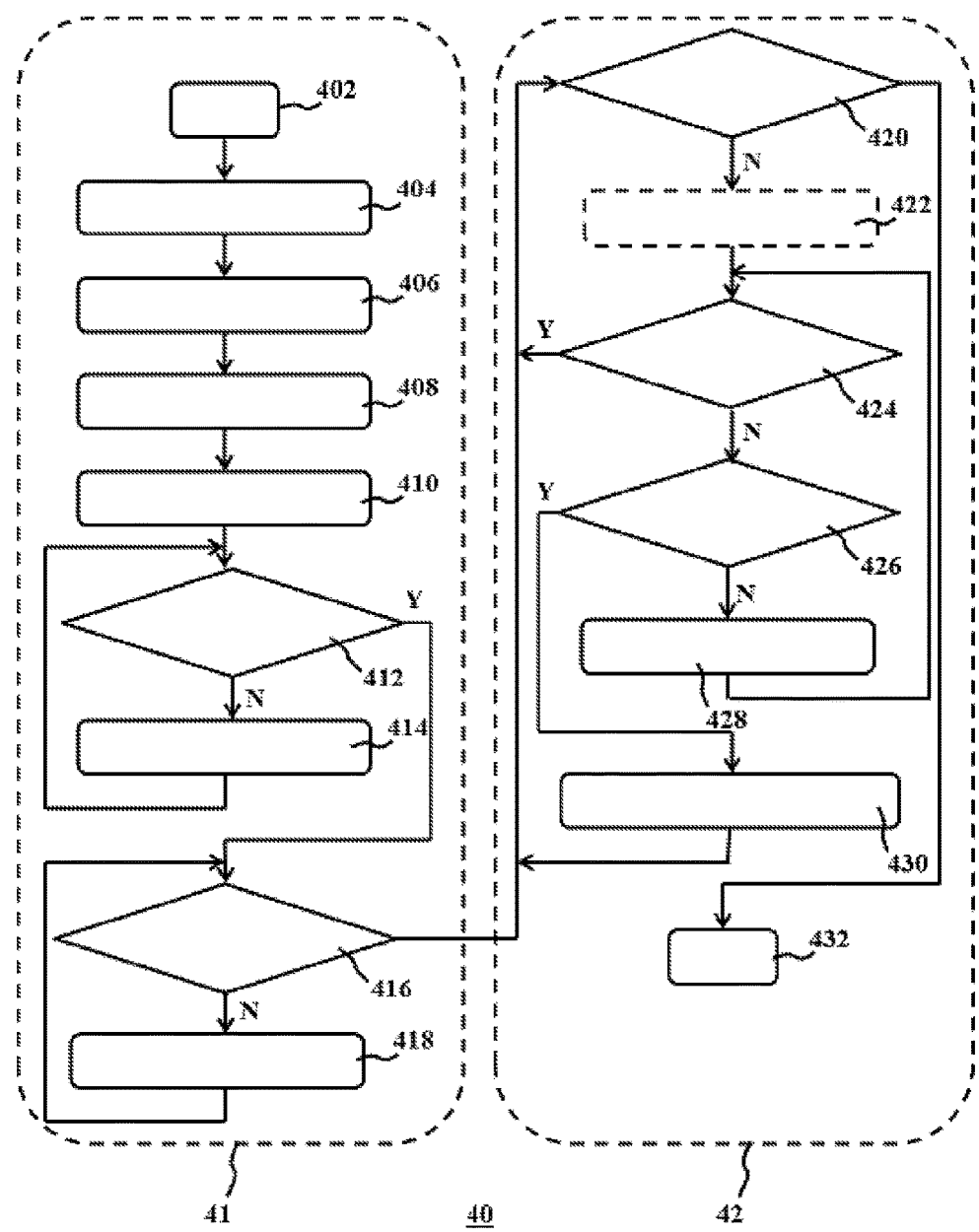
FIG. 4 is a flowchart of an embodiment of a CPR guidance method of the invention.
Figure 5:
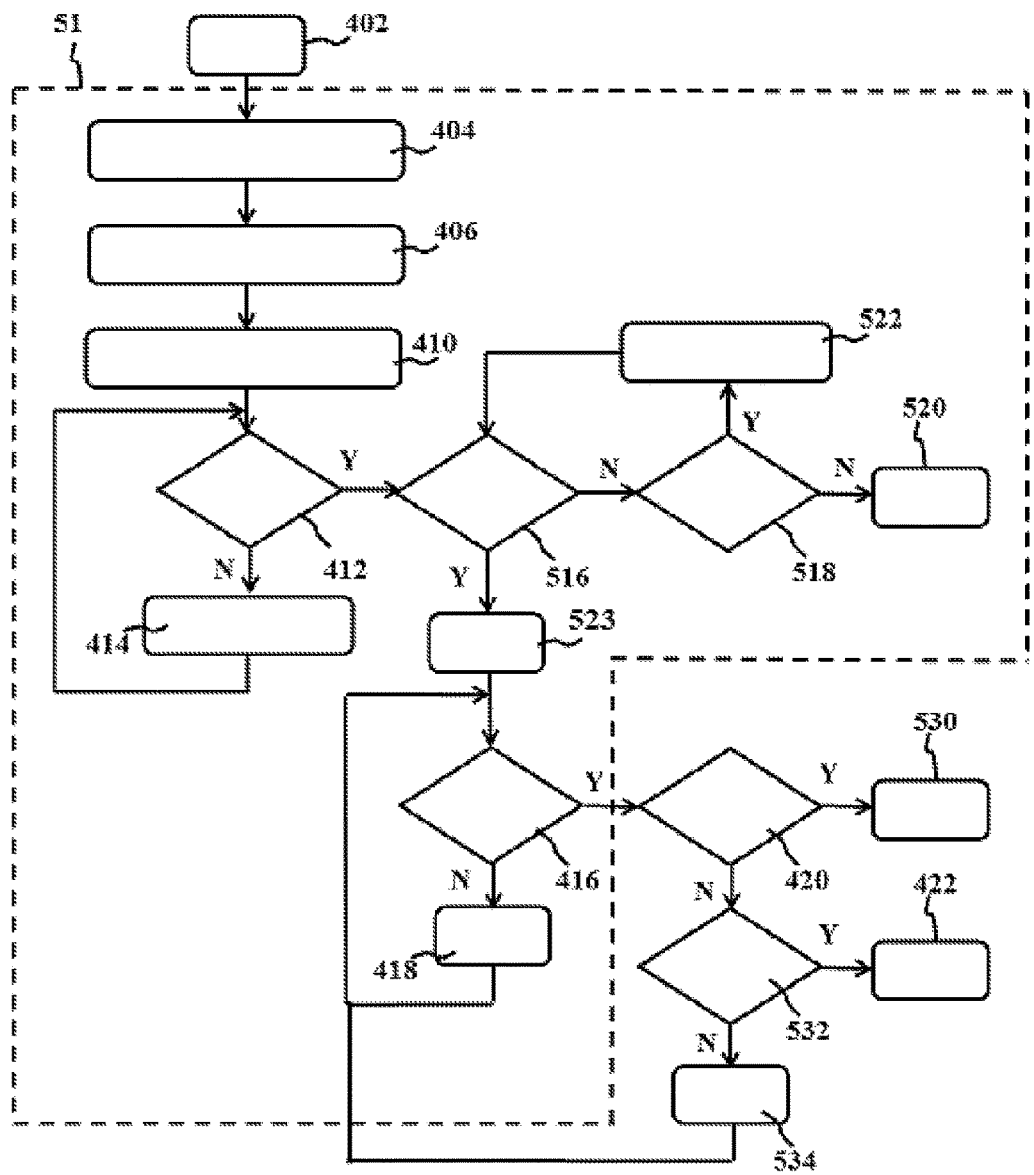
FIG. 5 is a flowchart of another embodiment of a CPR guidance method of the invention.

FIG. 5 depicts a flowchart of an example embodiment of a method 50 for providing CPR guidance using the CPR guidance system of the present invention. In a preferred embodiment, the method 50 comprises a first branch 51 in which sensor devices in the vicinity of the rescuer 20 are detected and added to the CPR guidance system, and a second branch in which the CPR guidance system is used to generate and present cardiopulmonary resuscitation guidance to a rescuer 20. As in the method 40 described in the context of FIG. 4, it is noted for the avoidance of doubt that the first branch 51 may be omitted from the method 50 in case of a head-mountable computing device 100 comprising the sensor 210 for monitoring vital signs of the victim 10, the sensor 310 for sensing an environment within which a victim is located, and the further sensor 300 for monitoring the chest compression characteristics caused by the administration of chest compressions to the victim 10 by the rescuer 20, and in which the CPR guidance system does not comprise any sensor 200 for monitoring vital signs of the victim 10 external to the head-mountable computing device 100.

The method 50 may start in step 402 by the discovery of a suspected victim of a SCA event by the rescuer 20 wearing the head-mountable computing device 100. In step 404 the head-mountable computing device 100 may be prompted to generate a first responder call to emergency services, in order to direct the emergency services to the location of the victim 10.

Next, the method 50 progresses to step 406 in which the head-mountable computing device 100 searches in the vicinity of the victim 10 for devices including a sensor 200 for detecting vital signs (such as breathing characteristics) of the victim or a sensor 310 for sensing the environment within which a victim is located.

In step 412 it is checked if the wireless connections between the identified devices and the head-mountable computing device 100 have been established. If for some reason some of the wireless connections have not been established, the method 50 proceeds to step 414 in which the rescuer 20 is alerted that some of the wireless connections could not be established, such that the rescuer 20 can attempt to adjust the affected devices, for instance by enabling a wireless communication mode of these devices.

Once all devices are wirelessly connected to the head-mountable computing device 100, the method 50 proceeds to step 516 in which a second signal conveying environmental information from at least one sensor is processed by the data processor 110 in order to extract the environmental information and to determine the existence of hazards or threats (such as fire, smoke, vehicle traffic, gas or chemical leaks, downed power lines or live electrical items, falling objects, etc.) in the vicinity of the victim 10 or rescuer 20. For example, data from a camera and microphone of a smartphone may be processed in accordance with image and sound classification algorithms incorporating face, object and sound recognition. This processing may be assisted by processing undertaken via a distributed processing environment (such as the 'cloud' for example). Also, additional environmental information may be provided from other services, e.g. traffic information, local weather conditions, location specific hazards stored in a database, and taken into account by the processing. Thus, in step 516, various types of environmental information, including: location information; traffic information; weather information; and hazard information may be processed by the data processor 110 to determine if there is a hazard or threat in the vicinity of the victim 10 or rescuer 20.

If it is determined that it is safe for the rescuer 20 to approach the victim 10, i.e. if no unacceptable hazards or threats are present, the method proceeds to step 523 in which the rescuer 20 guided to position the identified devices on or near the appropriate parts of the body of the victim 10 by way of placement instructions displayed on the at least one display module 106 (as will be described in more detail below).

If it is determined that it is not safe for the rescuer 20 to approach the victim 10, i.e. if unacceptable hazards or threats are present, the method proceeds to step 518 in which the data processor 110 determines if the hazard(s) or threat(s) can be safely managed, mitigated or avoided.

In case the data processor 110 determines that the environment within which the victim 10 is located comprises environmental hazards and/or threats that entirely prevent the safe administration of CPR (e.g. the situation is too dangerous to permit intervention), the method proceeds to step 520 in which the data processor 110 triggers the communication of guidance information advising the rescuer 20 of the potential dangers/threats and instructing the rescuer 20 to move to a safe nearby location to await emergency services arrival (e.g. using location information obtained by a sensor of the system).

In case the data processor 110 determines that the environment within which the victim 10 is located comprises environmental hazards and/or threats that may be avoided, managed or mitigated to enable the safe administration of CPR, the method proceeds to step 522 in which the data processor 110 triggers the communication of guidance information advising, via voice or visual prompts, how to mitigate the risk posed by the hazards by moving the victim for example. The method 50 then returns to step 516 to check if the hazard(s) or threat(s) still exist.

As detailed above, if it is determined in step 516 that it is safe for the rescuer 20 to approach the victim 10, i.e. if no unacceptable hazards or threats are present, the method proceeds to step 423 in which the rescuer 20 is subsequently guided to position the identified devices or sensors on or near the appropriate parts of the body of the victim 10 by way of placement instructions displayed on the at least one display module 106.

For example, in step 523, the rescuer 20 may be guided to place a device including a sensor 200 on the neck or on the forehead of the victim 10 such that the vital signs, e.g. pulse and breathing patterns, of the victim 10 can be detected, and to place a device including another sensor 300 on the chest of the victim 10 or on the hand or wrist of the rescuer 20 in order to provide the head-mountable computing device 100 with the sensor signals that will allow the CPR guidance system and in particular data processor 110 to generate CPR guidance as a function of the received sensor signals.

The method then proceeds to step 416 in which it is checked if all the devices are correctly positioned relative to the victim 10, e.g. are positioned in the correct positions on the body of the victim 10. If it is determined that the one or more sensors or devices are not positioned correctly, the method proceeds to step 418 in which the rescuer 20 is presented with positioning information for the incorrectly positioned sensor(s) or device(s).

Once all devices for providing the desired sensor data are correctly positioned, the method 50 proceeds to step 420 in which the data provided by the one or more devices comprising a sensor for monitoring vital signs of the victim 10 is analyzed by the data processor 110 to determine if the victim 10 requires CPR, i.e. to determine if the victim 10 has a pulse and is breathing.

In case the data processor 110 determines that the victim has a pulse and/or is breathing and does not require CPR, the method proceeds to step 530 in which the data processor 110 triggers the display of guidance information advising the rescuer 20 of the potential dangers/threats and instructing the rescuer 20 to change the position of the victim (e.g. place the victim 10 in a recovery position) and await emergency services arrival (e.g. using location information obtained by a sensor of the system). This may include presenting information on how to place the victim 10 in the recovery position on the at least one display module 106 of the head-mountable computing device 100.

In some embodiments, the method 50 may then loop back to step 516 or 420 to perform repeated monitoring of potential hazards in the vicinity of the victim and rescuer or of repeated monitoring of the vital signs of the victim. The method 50 may thus be continued until the emergency services arrive at the scene. This may for instance include continuing to monitor potential hazards and/or the vital signs of the victim 10 even after placing the victim 10 in the recovery position, for instance to detect another SCA event.

In case the data processor 110 determines that the victim does not have a pulse and/or is not breathing and does require CPR, the method 50 proceeds to step 532 in which a second signal conveying environmental information from at least one sensor is processed by the data processor 110 in order to extract the environmental information and to determine if the environmental conditions and/or terrain are suitable for the performance of effective CPR.

By way of example, this may be accomplished using images from the built-in camera and image processing algorithms to assess the lighting conditions, the inclination of the ground and suitability of the ground surface for compression during CPR, i.e., if the surface is too soft, rocky, uneven, inclined or unstable. Alternatively, this can be accomplished by a sensor or smart device (e.g., smart phone or smart watch) positioned directly on the victim's chest and then using the orientation of the built-in accelerometer to assess the inclination or unevenness of the ground and a motion classification algorithm to assess the instability and softness of the ground surface.

If, in step 532, it is determined that the victim is located in an area where the environmental conditions and/or terrain are unsuitable for the performance of effective CPR, e.g., if there is ice, mist, snow, poor light, or an inclined, unstable or uneven ground surface, etc., the method proceeds to step 534 in which the data processor 110 triggers the display of guidance information advising the rescuer 20 of the unsuitable environmental conditions and instructing the rescuer 20, via visual and/or audio prompts, to move the victim 10 to a nearby location which is suitable for CPR. The method then proceeds to step 416 in which it is checked once again if all the devices are correctly positioned relative to the victim 10, e.g. are positioned in the correct positions on the body of the victim 10.

If, in step 532, it is determined that the victim is located in an area where the environmental conditions and/or terrain are suitable for the performance of effective CPR, the method proceeds to step 422 in which the data processor 110 triggers the presentation of guidance information advising the rescuer 20 to initiate and continue CPR, and to the subsequents steps 424, 426, 428, 430 and 432 of the second branch 42 already described in the context of method 40 in FIG. 4.

In some embodiments, the method 50 may then loop back to step 420 to perform repeated monitoring of vital signs of the victim. In this manner, the method 50 may continue until the victim 10 exhibits a return to spontaneous circulation, e.g. exhibits spontaneous breathing and a life-sustaining pulse as detected in step 420, or until emergency services arrive on the scene to take over, upon which the method 50 may terminate by the rescuer 20 terminating CPR and placing the victim 10 in the recovery position.

Other suitable extensions and variations to the above disclosed embodiments will be apparent to the skilled person.

Aspects of the present invention may be embodied as a cardiopulmonary resuscitation guidance method or system at least partially embodied by a head-mountable computing device or distributed over separate entities including a head-mountable computing device. Aspects of the present invention may take the form of a computer program product embodied in one or more computer-readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Such a system, apparatus or device may be accessible over any suitable network connection; for instance, the system, apparatus or device may be accessible over a network for retrieval of the computer readable program code over the network. Such a network may for instance be the Internet, a mobile communications network or the like. More specific examples (a non-exhaustive list) of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of the present application, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out the methods of the present invention by execution on the processor 110 may be written in any combination of one or more programming languages, including an object oriented programming language such as Java, Smalltalk, C++ or the like and conventional procedural programming languages, such as the "C" programming language or similar programming languages. The program code may execute entirely on the processor 110 as a stand-alone software package, e.g. an app, or may be executed partly on the processor 110 and partly on a remote server. In the latter scenario, the remote server may be connected to the head-mountable computing device 100 through any type of network, including a local area network (LAN) or a wide area network (WAN), or the connection may be made to an external computer, e.g. through the Internet using an Internet Service Provider.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions to be executed in whole or in part on the display processor 108 and/or the data processor 110 of the cardiopulmonary resuscitation guidance system including the head-mountable computing device 100, such that the instructions create means for implementing the functions/acts specified in the flowchart and/or block diagram block or blocks. These computer program instructions may also be stored in a computer-readable medium that can direct the cardiopulmonary resuscitation guidance system including the head-mountable computing device 100 to function in a particular manner.

The computer program instructions may be loaded onto the display processor 108 and/or the data processor 110 to cause a series of operational steps to be performed on the display processor 108 and/or the data processor 110, to produce a computer-implemented process such that the instructions which execute on the display processor 108 and/or the data processor 110 provide processes for implementing the functions/acts specified in the flowchart and/or block diagram block or blocks. The computer program product may form part of a cardiopulmonary resuscitation guidance system including the head-mountable computing device 100, e.g. may be installed on the cardiopulmonary resuscitation guidance system.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A cardiopulmonary resuscitation guidance method for a system including a head-mountable computing device that comprises a processor and at least one display module arranged to be viewed by a wearer of the head-mountable computing device when wearing the device, the method comprising:

receiving, at said processor, a first signal conveying vital signs information from at least one sensor for monitoring vital signs of a patient or victim, wherein a sensor of the at least one sensor is integrated in the head-mountable computing device;

processing, via said processor, said first signal to extract the vital signs information; and displaying, via said at least one display module, cardiopulmonary resuscitation guidance in response to the processed vital signs information, the method further comprising:

receiving, at said processor, a second signal conveying environmental information from at least one sensor for sensing an environment within which the patient or victim is located;

processing, via said processor, said second signal to extract the environmental information for assessing and identifying environmental conditions, hazards and terrain challenges (i) which pose a threat to a safety of the wearer or the victim and (ii) which adversely affect a delivery of effective cardiopulmonary resuscitation; and displaying, via the at least one display module, adjusted cardiopulmonary resuscitation guidance in response to the extracted environmental information, wherein the adjusted cardiopulmonary resuscitation guidance includes guidance (i) to mitigate or avoid the identified hazards, and (ii) to manage the identified environmental conditions and terrain challenges to ensure safe and effective cardiopulmonary resuscitation.

2. The method of claim 1, wherein said vital signs information comprises at least one of breathing information and pulse information.

3. The method of claim 1, further comprising:
receiving, on said processor, patient chest compression characteristics from a further sensor for detecting said patient chest compression characteristics;
processing said chest compression characteristics on said processor; and
displaying adjusted cardiopulmonary resuscitation guidance in response to the processed patient chest compression characteristics.

4. The method of claim 3, wherein displaying adjusted cardiopulmonary resuscitation guidance comprises displaying a suggested change of administrator of the cardiopulmonary resuscitation in response to a gradual decline in at least one of chest compression depth and chest compression frequency.

5. The method of claim 1, further comprising:
automatically identifying devices for wirelessly communicating with the head-mountable computing device, wherein each of said devices comprise at least one of a sensor for monitoring vital signs of a patient and a further sensor for detecting patient chest compression characteristics; and
wirelessly connecting selected identified devices to the head-mountable computing device.

6. The method of claim 5, further comprising generating an alert on the at least one display module for alerting a wearer of the head-mountable computing device to enable a wireless communication mode of an identified device.

7. The method of claim 5, further comprising displaying positioning information for positioning the selected identified devices on the patient on the at least one display module.

8. The method of claim 1, further comprising:
automatically identifying a defibrillator device in the vicinity of the patient; and
providing user instructions for said defibrillator device on the at least one display device.

9. The method of claim 1, further comprising:
automatically connecting to a remote emergency service with said system; and
sending a distress signal to said service with said system, said signal including global positioning information.

10. The method of claim 1, wherein said environmental information comprises:
location information;
traffic information;
weather information; and
hazard information.

11. The method of claim 1, wherein displaying adjusted cardiopulmonary resuscitation guidance comprises:
displaying a suggested change of location of the victim in response to the processed environmental information.

12. The method of claim 1, wherein displaying adjusted cardiopulmonary resuscitation guidance comprises displaying a suggested change of position of the victim in response to the vital signs information indicating that the victim has a pulse and/or is breathing.

13. The method of claim 1, wherein displaying adjusted cardiopulmonary resuscitation guidance comprises displaying a suggested change of location of the victim in response to (i) the vital signs information indicating that the victim does not have a pulse and/or is not breathing and (ii) further based on the processed environmental information.

14. The method of claim 1, further comprising:
automatically identifying devices for wirelessly communicating with the head-mountable computing device, wherein each of said devices comprise at least one of a sensor for sensing an environment within which the victim is located; and
wirelessly connecting selected identified devices to the head-mountable computing device.

15. A non-transitory computer-readable medium embodied with computer program code for implementing the method of claim 1 when executed on the processor of the head-mountable computing device that further includes at least one display module arranged to be viewed by the wearer of the head-mountable computing device when wearing the device.

16. A cardiopulmonary resuscitation guidance system including the non-transitory computer-readable medium of claim 15 and the head-mountable computing device comprising:
the sensor for monitoring vital signs of the patient, at least one display module arranged to be viewed by the wearer of the head-mountable computing device when wearing the device, and the processor adapted to execute the computer program code of said non-transitory computer-readable medium.

17. The cardiopulmonary resuscitation guidance system of claim 16, further comprising one or more of the at least one sensor for monitoring vital signs of the patient external to the head-mountable computing device.

18. The cardiopulmonary resuscitation guidance system of claim 16, further comprising at least one of a sensor for sensing an environment within which the victim is located.

19. The cardiopulmonary resuscitation guidance system of claim 16, further comprising a further sensor for detecting patient chest compression characteristics.

20. The cardiopulmonary resuscitation guidance system of claim 19, wherein the further sensor is integrated in a portable or wearable device that includes one or more of a smart phone or smart watch.

* * * * *